(12) United States Patent
Lu et al.

(10) Patent No.: US 9,408,917 B2
(45) Date of Patent: Aug. 9, 2016

(54) PHARMACEUTICAL COMPOSITION

(71) Applicant: Industrial Technology Research Institute, Hsinchu (TW)

(72) Inventors: Maggie J. M. Lu, Jhudong Township, Hsinchu County (TW); Yu-Wen Lo, Shueishang Township, Chiayi County (TW); Chih-Peng Liu, Hsinchu (TW); Chia-Wen Huang, Hukou Township, Hsinchu County (TW); Shuen-Hsiang Chou, Zhunan Township, Miaoli County (TW); Po-Hung Lai, New Taipei (TW); Tsan-Lin Hu, Jhubei (TW); Min-Ying Lin, Hsinchu (TW); Chia-Mu Tu, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 13/926,363

(22) Filed: Jun. 25, 2013

(65) Prior Publication Data

US 2014/0199369 A1 Jul. 17, 2014

(30) Foreign Application Priority Data

Jan. 17, 2013 (TW) .............................. 102101736 A (51) Int. Cl.
*A61K 47/36* (2006.01)
*A61K 9/00* (2006.01)
*A61K 9/127* (2006.01)

(52) U.S. Cl.
CPC ............... *A61K 47/36* (2013.01); *A61K 9/0024* (2013.01); *A61K 9/0085* (2013.01); *A61K 9/127* (2013.01)

(58) Field of Classification Search
None
See application file for complete search history.

(56) References Cited

U.S. PATENT DOCUMENTS

| | | | |
|---|---|---|---|
| 7,098,194 B2 | 8/2006 | Chenite et al. | |
| 8,119,102 B1 * | 2/2012 | Sung et al. | 424/1.69 |
| 8,187,571 B1 * | 5/2012 | Sung et al. | 424/1.73 |
| 8,257,740 B1 | 9/2012 | Sung et al. | |
| 8,263,130 B2 | 9/2012 | Chen et al. | |
| 8,283,317 B1 | 10/2012 | Sung et al. | |
| 8,287,905 B1 | 10/2012 | Sung et al. | |
| 8,354,094 B1 * | 1/2013 | Sung et al. | 424/1.73 |
| 2004/0225077 A1 * | 11/2004 | Gravett et al. | 525/418 |
| 2005/0019404 A1 | 1/2005 | Sung et al. | |
| 2005/0208122 A1 | 9/2005 | Allen et al. | |
| 2008/0008755 A1 | 1/2008 | Kwon et al. | |
| 2008/0248991 A1 * | 10/2008 | Dyer et al. | 514/2 |
| 2009/0076177 A1 * | 3/2009 | Bausch | A61K 9/146 514/785 |
| 2009/0118480 A1 | 5/2009 | Holappa et al. | |
| 2010/0203163 A1 | 8/2010 | Allen | |
| 2012/0065614 A1 | 3/2012 | Omary et al. | |

FOREIGN PATENT DOCUMENTS

| | | | |
|---|---|---|---|
| EP | 2 294 126 A1 | 3/2011 | |
| TW | 201016223 A1 | 5/2010 | |
| WO | WO 2009/150651 A1 | 12/2009 | |
| WO | WO-2013-063263 | * | 5/2013 |

OTHER PUBLICATIONS

Kumbar S, synthesis and characterization of modified chitosan microspheres: effect of the grafting ratio on the controlled release of nifedipine through microspheres, journal of applied polymer science, 89, 2940-2949, 2003.*
Khan, I, Assessment of palmitoyl and sulphate conjugated glycol chitosan for development of polymeric micelles, 2013, 3(2), 97-100.*
Chiu et al., "pH-triggered injectable hydrogels prepared from aqueous N-palitoyl chitosan: In vitro characteristics and in vivo biocompatibility," Biomaterials, vol. 30, pp. 4877-4888 (2009).
Bhattarai et al., "PEG-grafted chitosan as an injectable thermosensitive hydrogel for sustained protein release," J. of Controlled Release, vol. 103, pp. 609-624 (2005).
Li et al., "A Novel Composite Hydrogel Based on Chitosan and Inorganic Phosphate for Local Drug Delivery of Camptothecin Nanocolloids," J. of Pharmaceutical Sciences, vol. 100, No. 1, pp. 232-241 (Jan. 2011).
Wu et al., "A thermo- and pH-sensitive hydrogel composed of quaternized chitosan/glycerophosphate," Int'l J. of Pharma., vol. 315, pp. 1-11 (2006).
Ruel-Gariépy et al., "A thermosensitive chitosan-based hydrogel for the local delivery of paclitaxel," Eur. J. of Pharma. & Biopharma., vol. 57, pp. 53-63 (2004).
Fujita et al., "Vascularization in vivo caused by the controlled release of fibroblast growth factor-2 from an injectable chitosan/non-anticoagulant heparin hydrogel," Biomaterials, vol. 25, pp. 699-706 (2004).
Yang et al., "Chitosan/Gelatin Hydrogel Prolonged the Function of Insulinoma/Agarose Microspheres In Vivo During Xenogenic Transplantation," Transplantation Proc., vol. 40, pp. 3623-3626 (2008).
Cheng et al., "Thermosensitive chitosan-gelatin-glycerol phosphate hydrogel as a controlled release system of ferulic acid for nucleus pulposus regeneration," Biomaterials, vol. 32, pp. 6953-6961 (2011).
Chiu et al., "Controlled release of thymosin β4 using collagen-chitosan composite hydrogels promotes epicardial cell migration and angiogenesis," J. of Controlled Release, vol. 155, pp. 376-385 (2011).

(Continued)

Primary Examiner — Frederick Krass
Assistant Examiner — Celeste A Roney
(74) Attorney, Agent, or Firm — Muncy, Geissler, Olds & Lowe, P.C.

(57) ABSTRACT

The disclosure provides a pharmaceutical composition. The pharmaceutical composition includes a chitosan with palmitoyl groups and an active agent. According to another embodiment, the pharmaceutical composition can further include a gelling accelerating agent. According to an embodiment of the disclosure, the active agent of the disclosure can be administered in the form of a nano-drug, liposome, micelle, or microparticle.

7 Claims, 8 Drawing Sheets

(56) References Cited

OTHER PUBLICATIONS

Fang et al., "Temperature-sensitive hydrogels composed of chitosan and hyaluronic acid as injectable carriers for drug delivery," Eur. J. of Pharma. & Biopharma., vol. 68, pp. 626-636 (2008).

Nakamura et al., "Effect of controlled release of fibroblast growth factor-2 from chitosan/fucoidan micro complex-hydrogel on in vitro and in vivo vascularization," J. of Biomed. Mat. Res., Part A, pp. 619-627 (2007).

Tran et al., "In Situ Forming and Rutin-Releasing Chitosan Hydrogels as Injectable Dressings for Dermal Wound Healing," Biomacromolecules, vol. 12, pp. 2872-2880 (2011).

Ji et al., "A novel injectable chlorhexidine thermosensitive hydrogel for periodontal application: preparation, antibacterial activity and toxicity evaluation," J. Mater. Sci.: Mater. Med., vol. 21, pp. 2435-2442 (2010).

Kim et al., "A chitosan/$\beta$-glycerophosphate thermo-sensitive gel for the delivery of ellagic acid for the treatment of brain cancer," Biomaterials, vol. 31, pp. 4157-4166 (2010).

Liu et al., "Smart gelation of chitosan solution in the presence of $NaHCO_3$ for injectable drug delivery system," Int'l J. of Pharma., vol. 414, pp. 6-15 (2011).

Chen et al., "A novel pH-sensitive hydrogel composed of N,O-carboxymethyl chitosan and alginate cross-linked by genipin for protein drug delivery," J. of Controlled Release, vol. 96, pp. 285-300 (2004).

Tan et al., "Injectable in situ forming biodegradable chitosan-hyaluronic acid based hydrogels for adipose tissue regeneration," Organogenesis, vol. 6.3, pp. 173-180 (2010).

Lo et al., "In Situ Hydrogel for the Sustained Release of Anti-Cancer Drug," 39th Ann. Meeting & Expo of the Controlled Release Soc. (CRS), pp. 1-2 (Jul. 17, 2012).

Taiwan Office Action for Taiwan Application No. 102101736 dated Aug. 22, 2014.

* cited by examiner

PHARMACEUTICAL COMPOSITION

CROSS REFERENCE TO RELATED APPLICATIONS

This application is based upon and claims the benefit of priority from the prior Taiwan Patent Application No. 102101736, filed on Jan. 17, 2013, the entire contents of which are incorporated herein by reference.

TECHNICAL FIELD

The disclosure relates to a pharmaceutical composition and, more particularly, to an injectable pharmaceutical composition with a long-term release characteristic.

BACKGROUND

Bioactive substance (e.g. drugs, growth factors, nucleic acids etc.) delivery is very important in the biomedical applications which comprise tissue engineering, cell therapy and pharmaceutical therapy. The materials for the delivery carriers must provide biocompatible and biodegradable properties for feasible implantation. Preferably, the material is a fluid ex vivo for easy mixing with drugs and transformation into a gel after being injected into the body by a syringe, catheter or laparoscope for delivering bioactive substances to desired tissue areas. After, the drugs are released over time, achieving therapeutic effects.

There is, therefore, a need for a novel pharmaceutical composition having long-term release and injectability characteristics, in order to effectively make an active agent of a pharmaceutical composition arrive at an affected tissue area.

BRIEF SUMMARY

An exemplary embodiment of the disclosure provides a pharmaceutical composition, including a chitosan with palmitoyl groups, and an active agent. According to an embodiment of the disclosure, the active agent of the disclosure can be administered in the form of a nano-drug, liposome, micelle, or microparticle. Further, according to another embodiment of the disclosure, the pharmaceutical composition of the disclosure can include a chitosan with palmitoyl groups, an active agent, and a gelling accelerating agent.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

The disclosure provides a pharmaceutical composition employing a hydrophobically modified chitosan for carrying an active agent (which can be fabricated in a specific form in advance). The pharmaceutical composition of the disclosure can serve as a pH-responsive hydrogel system and be in-situ triggered by environmental stimuli and implemented as an injectable delivery system for various biomedical applications, such as drug delivery.

According to an embodiment of the disclosure, the pharmaceutical composition includes a chitosan with palmitoyl groups, and an active agent. Particularly, the chitosan with palmitoyl groups had a weight percentage of 50-98.5 wt %, and an active agent having a weight percentage of 1.5-50 wt %, based on the total weight of the chitosan with palmitoyl groups and the active agent.

The chitosan with palmitoyl groups can be prepared by graft-modifying a chitosan with the palmitic acid N-hydroxysuccinimide ester, obtaining the hydrophobically modified chitosan.

When reacting the chitosan with the palmitic acid N-hydroxysuccinimide ester, one hydrogen atom bonded onto a nitrogen atom of the repeat unit (having a structure represented by of the chitosan is replaced with a palmitoyl group, forming a new repeat unit (having a structure represented by According to embodiments of the disclosure, the chitosan with palmitoyl groups of the disclosure can be a chitosan grafted with palmitic acid N-hydroxysuccinimide ester at a grafting ratio of 5-25%, such as 5-22%. Herein, the term "grafting ratio" means the percentage of the hydrogen atoms of the chitosan replaced with the palmitoyl groups. In detail, when the chitosan has N number of repeat units (N>1) before modification, and the modified chitosan has X number of repeat units (N>X>0) after modifying the chitosan with the palmitic acid N-hydroxysucc nimide ester, the grafting ratio (G) can be defined by the following equation:

$$G = X/N \times 100\%$$

The grafting rate of the chitosan with palmitoyl groups can be determined by a Ninhydrin assay, and includes the following steps. First, the chitosan with palmitoyl groups is dissolved in an acetic acid aqueous solution (1%). After stirring for 24 hrs, the mixture, a buffer solution (acetic acid/acetate, 4M, with a pH 5.5), and a Ninhydrin agent are added into a test tube. After reacting at 100° C. for 20 min, the absorbance value (at 570 nm) of the solution in the test tube is determined, and the result is compared with a blank group (the buffer solution) and a control group (the solution including non-modified chitosan, the buffer solution and the Ninhydrin agent).

The active agent can include a hydrophilic active agent, hydrophobic active agent, or combinations thereof. For example, the hydrophobic active agent can be paclitaxel, docetaxel, or combinations thereof. The hydrophilic active agent can be cisplatin, doxorubicin, bovine serum albumin, immunoglobulin G (IgG), or combinations thereof. Further, the active agent can be administered in the form of a drug powder, drug solution, nano-drug, liposome, micelle, or microparticle.

According to another embodiment of the disclosure, the pharmaceutical composition can include a chitosan with palmitoyl groups, an active agent, and a gelling accelerating agent. Particularly, the pharmaceutical composition can include 2-120 parts by weight of a gelling accelerating agent and 100 parts by weight of the sum of the chitosan with palmitoyl groups and the active agent.

The gelling accelerating agent can enhance the gelation rate of the pharmaceutical composition (including the chitosan with palmitoyl groups and active agent) when triggered by a specific environmental pH value.

Further, according to some embodiments of the disclosure, the pharmaceutical composition having a gelling accelerating agent can also have advantages of extended release time and biocompatibility. The gelling accelerating agent can include a negatively charged material, electrically neutral material, hydrophobic material, or combinations thereof. For example, when the gelling accelerating agent is a negatively charged material (such as a sodium dodecyl sulfate, polyacrylic acid, sodium triphosphate, γ-Poly glutamic acid, β-glycerophosphate, or combinations thereof), the gelation rate of the pharmaceutical composition can be enhanced due to the ionic crosslink produced by the negative charges of the negatively charged material and the positive charges of the modified chitosan.

Further, when the gelling accelerating agent is an electrically neutral material (such as glycerol), the gelling accelerating agent can promote the pharmaceutical composition to form a hydrogel due to the hydrogen bonding interaction therebetween. Moreover, when the gelling accelerating agent is a hydrophobic material (such as a lipid), the biocompatibility of the pharmaceutical composition can be improved thereby.

The pharmaceutical composition of the disclosure can be used in a broad range of applications such as for the treatment of cancer, schizophrenia, rheumatoid arthritis, or hormone deficient disease. Further, the pharmaceutical composition can be administered by brain implantation, intraperitoneal injection, intramuscular injection, or subcutaneous injection.

It should be noted that, due to the cohesion between the molecules of the pharmaceutical composition provided by the hydrophobic groups (palmitoyl groups) of the modified chitosan and the pH sensitive chitosan, the pharmaceutical composition can be rapidly transformed into hydrogel and be triggered by environmental pH. Also, the pharmaceutical composition of the disclosure including the active agent has long-term release characteristics due to the ionic charges and hydrophobic interaction. Herein, the term "long-term release characteristics" mean the active agent of the pharmaceutical composition of the disclosure had a relatively long release time in comparison with the active agent which is not together with a carrier.

Further, since the pharmaceutical composition can administer the active agent in the form of a drug powder, drug solution, nano-drug, liposome, micelle, or microparticle, the pharmaceutical composition exhibits high drug delivery efficiency.

Further, the pharmaceutical composition of the disclosure can further include a gelling accelerating agent, thereby enhancing the gelation rate, extending the release time, and, improving the biocompatibility of the pharmaceutical composition.

The following examples are intended to illustrate the disclosure more fully without limiting its scope, since numerous modifications and variations will be apparent to those skilled in this art.

Example 1

1 g of chitosan with palmitoyl groups (with a grafting rate of 15%, and a molecular weight of 500 kDa) was dissolved in 100 mL of an acetic acid aqueous solution (1%). After dialysis, the pH value of the mixture was close to pH 6.2~6.5. After ultrafiltration, a solution was obtained, wherein the chitosan with palmitoyl groups had a weight percentage of 0.8 wt %. Next, 50 mg of paclitaxel was dissolved in 1 mL of ethanol, obtaining the solution including paclitaxel. Next, the solution including paclitaxel and the solution including the modified chitosan were mixed to obtain a pharmaceutical composition (1) (with a paclitaxel concentration of 5 mg/mL), wherein the volume ratio of the solution including paclitaxel and the solution including the modified chitosan was 1:9. The components of the pharmaceutical composition (1) are shown in Table 1.

Figure 1:
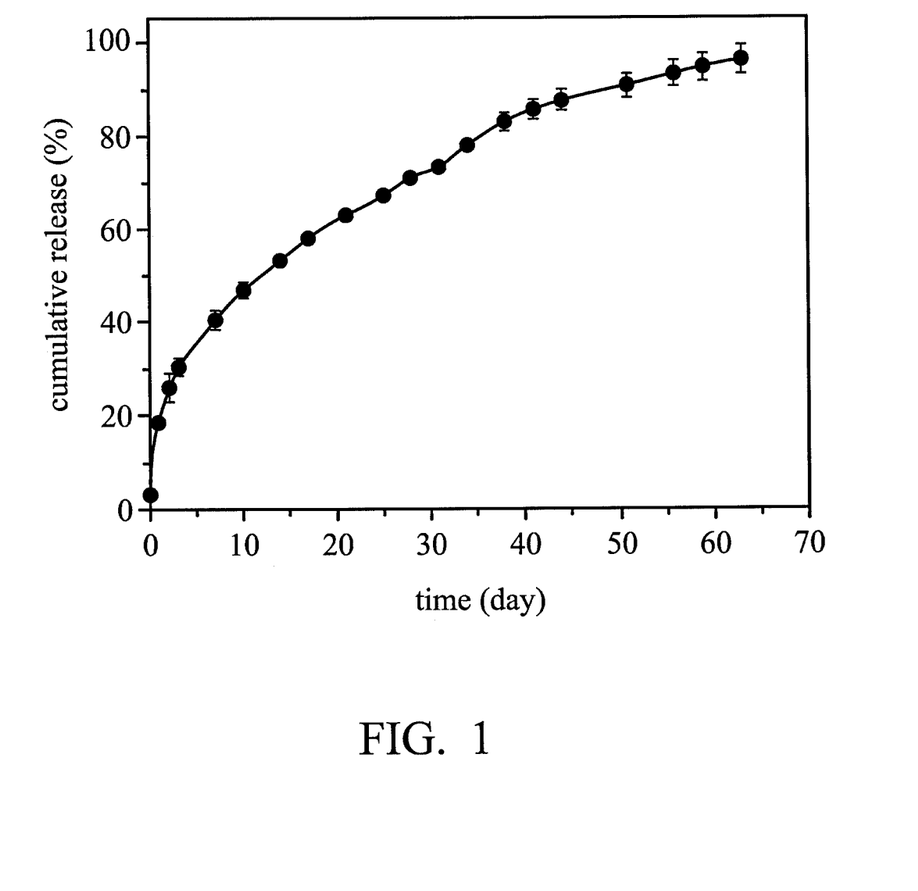
FIG. 1 shows a graph plotting cumulative release against time of the pharmaceutical composition of Example 1.

The cumulative release dose of the pharmaceutical composition (1) was measured by following steps. 500 μL of pharmaceutical composition (1) was loaded into circular-shaped tube and then added with the 5 mL release medium which comprised of 10 mM PBS (pH 7.4) containing 2.4% polysorbate 80 (manufactured by Scharlau with the trade No. of Tween 80) and 4% polyoxyethylene castor oil (manufactured by Sigma with the trade No. of Cremophor EL). The bottles were placed in a shaking incubator at 37° C. and 25 rpm. At different time periods, 5 mL release medium was analyzed for drug concentration via HPLC. The release medium was replaced with fresh media after each removal. The pharmaceutical composition (1) had a long-term release characteristic of more than 60 days (FIG. 1).

Figure 2:
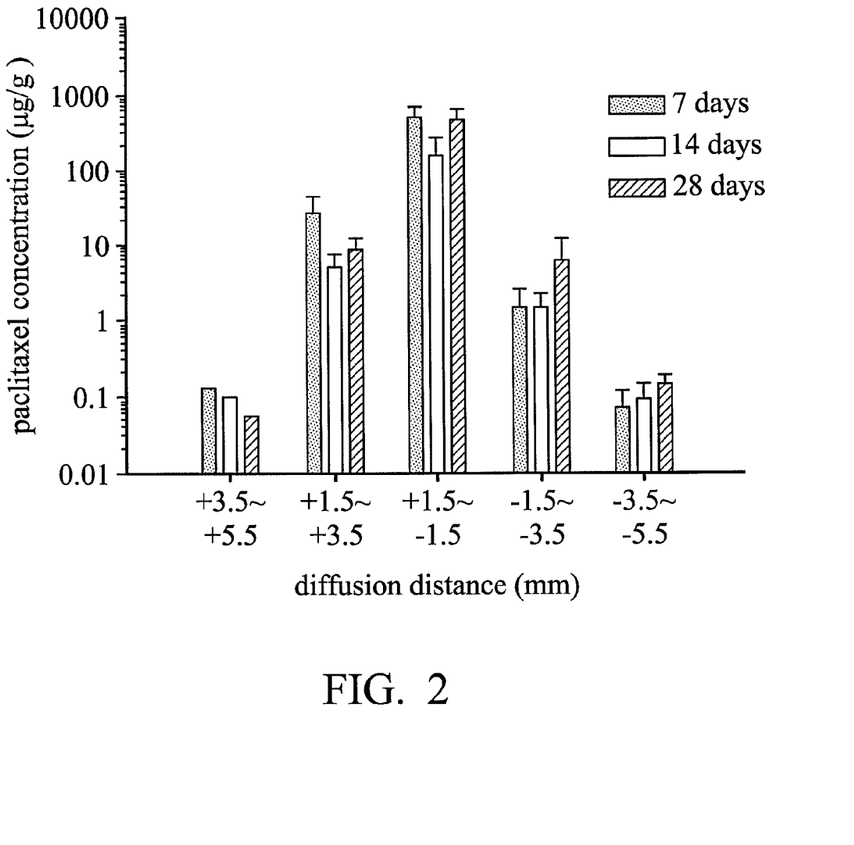
FIG. 2 shows a graph plotting diffusion distance against paclitaxel concentration after injecting the pharmaceutical composition of Example 1 into the brain tissue of rat.

Further, the pharmaceutical composition (1) was injected into the brain of a rat, and the diffusion of the drug was respectively observed at 7, 14, and 28 days. As shown in FIG. 2, the paclitaxel released by the pharmaceutical composition was detected even after 28 days.

Example 2

1 g of chitosan with palmitoyl groups (with a grafting rate of 12%, and a molecular weight of 500 kDa) was dissolved in 100 mL of an acetic acid aqueous solution (1%). After dialysis, the pH value of the mixture was close to pH 6.2~6.5. After ultrafiltration, a solution was obtained, wherein the chitosan with palmitoyl groups had a weight percentage of 0.72 wt %. Next, 10 mg of paclitaxel (nano-crystal) was added into 2 mL of the solution including chitosan with palmitoyl groups. After stirring, a pharmaceutical composition (2) (with a paclitaxel concentration of 5 mg/mL) was obtained. The components of the pharmaceutical composition (2) are shown in Table 1.

Figure 3:
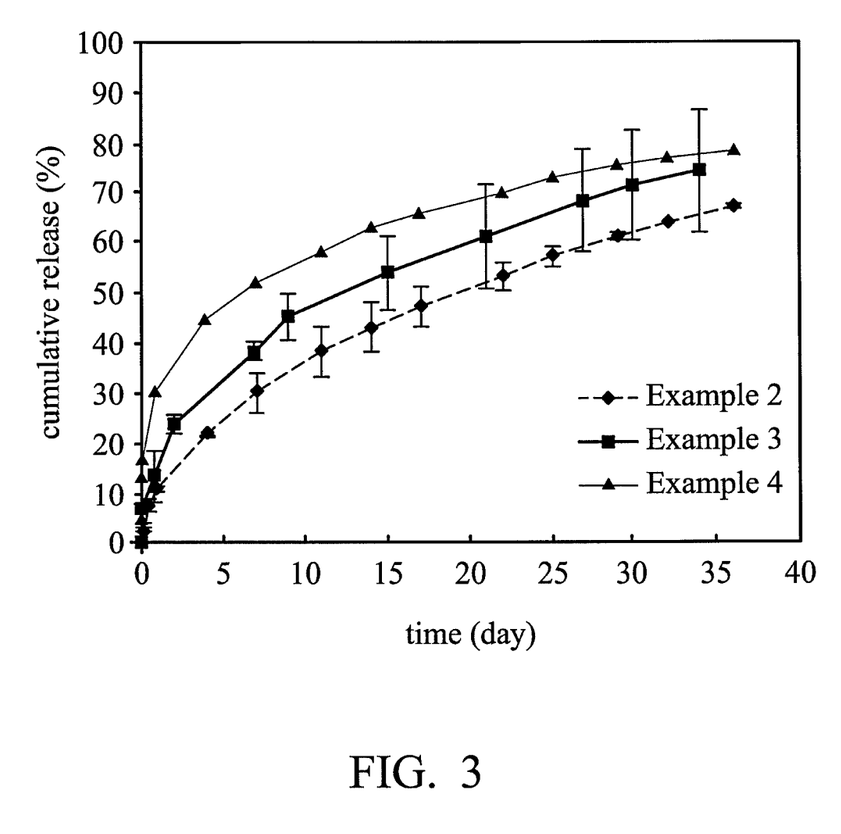
FIG. 3 shows a graph plotting cumulative release against time of the pharmaceutical compositions of Examples 2-4.

The cumulative release dose of the pharmaceutical composition (2) was measured according to the method as disclosed in Example 1, and the result is shown in FIG. 3. As shown in FIG. 3, the pharmaceutical composition (2) had a long-term release characteristic of more than 35 days.

The pharmaceutical composition (2) was injected into the peritoneal cavity of a rat, and the paclitaxel (with a concentration of 0.4-30 μg per gram of tissue) released by the pharmaceutical composition was detected even after 28 days.

Example 3

Example 3 was performed as Example 2 except that the concentration of the chitosan with palmitoyl groups was reduced from 0.72 wt % to 0.6 wt %, obtaining the pharmaceutical composition (3). The components of the pharmaceutical composition (3) are shown in Table 1.

The cumulative release dose of the pharmaceutical composition (3) was measured according to the method as disclosed in Example 1, and the result is shown in FIG. 3. As shown in FIG. 3, the pharmaceutical composition (3) had a long-term release characteristic of more than 35 days.

Example 4

Example 4 was performed as Example 2 except that the concentration of the chitosan with palmitoyl groups was reduced from 0.72 wt % to 0.5 wt %, obtaining the pharmaceutical composition (4). The components of the pharmaceutical composition (4) are shown in Table 1.

The cumulative release dose of the pharmaceutical composition (4) was measured according to the method as disclosed in Example 1, and the result is shown in FIG. 3. As shown in FIG. 3, the pharmaceutical composition (4) had a long-term release characteristic of more than 35 days.

Example 5

1 g of chitosan with palmitoyl groups (with a grafting rate of 15%, and a molecular weight of 500 kDa) was dissolved in 100 mL of an acetic acid aqueous solution (1%). After dialysis, the pH value of the mixture was close to pH 6.26.5. After ultrafiltration, a solution was obtained, wherein the chitosan with palmitoyl groups had a weight percentage of 0.8 wt %. Next, a doxorubicin liposome solution (1.4 mg/mL) (the preparation of the doxorubicin liposome solution was as disclosed in TW Pat. I262798, and U.S. application Ser. No. 12/076,294) was mixed with the solution including chitosan with palmitoyl groups, obtaining the pharmaceutical composition (5) (with a doxorubicin concentration of 0.14 mg/mL). Particularly, the volume ratio of the doxorubicin liposome solution and the solution including the modified chitosan was 1:9. The components of the pharmaceutical composition (5) are shown in Table 1.

Figure 4:
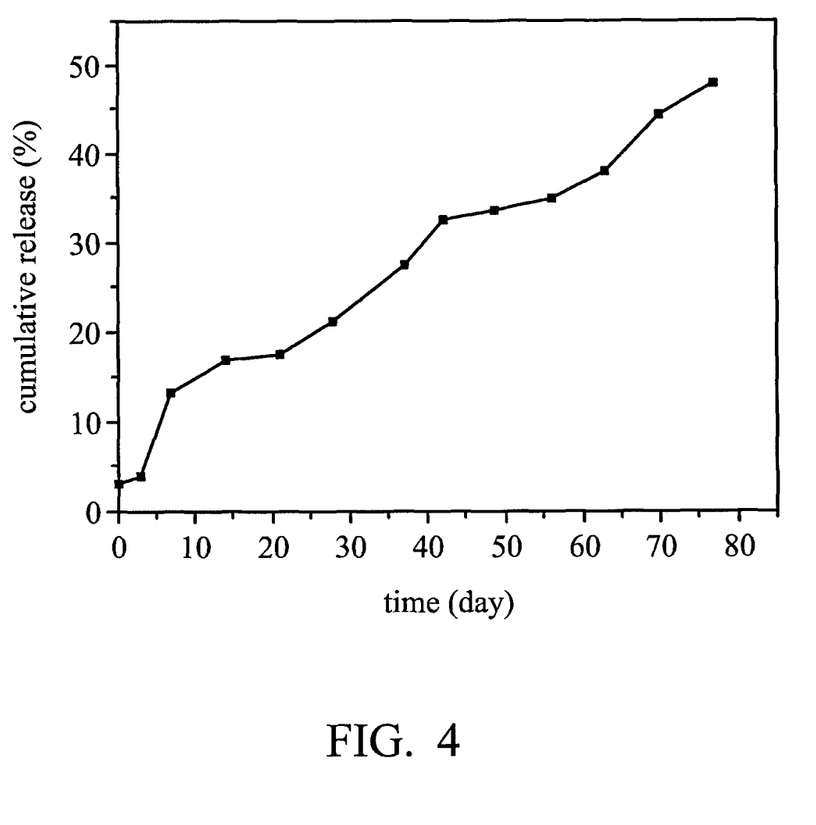
FIG. 4 shows a graph plotting cumulative release against time of the pharmaceutical composition of Example 5.

The cumulative release dose of the pharmaceutical composition (5) was measured according to the method as disclosed in Example 1 (10 mM PBS (pH 7.4) as the release medium), and the results are shown in FIG. 4. The pharmaceutical composition (5) had a long-term release characteristic of more than 80 days.

Figure 5:
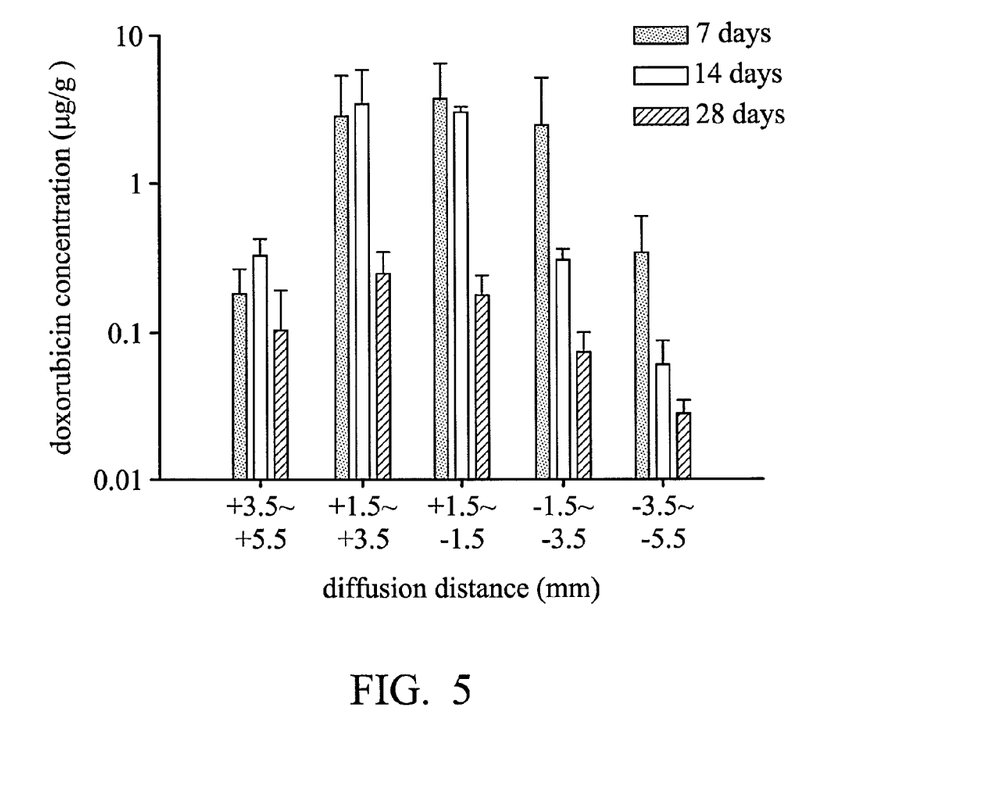
FIG. 5 shows a graph plotting diffusion distance against doxorubicin concentration after injecting the pharmaceutical composition of Example 5 into the brain tissue of rat.

Further, the pharmaceutical composition (5) was injected into the brain of a rat, and the diffusion of the drug was respectively observed at 7, 14, and 28 days. As shown in FIG. 5, the doxorubicin released by the pharmaceutical composition was detected even after 28 days.

Example 6

1 g of chitosan with palmitoyl groups (with a grafting rate of 20%, and a molecular weight of 500 kDa) was dissolved in 100 mL of an acetic acid aqueous solution (1%). After dialysis, the pH value of the mixture was close to pH 6.2~6.5. After ultrafiltration, a solution was obtained, wherein the chitosan with palmitoyl groups had a weight percentage of 0.72 wt %. Next, 10 mg of bovine serum albumin powder was mixed with 2 mL of the solution including chitosan with palmitoyl groups, obtaining the pharmaceutical composition (6) (with a bovine serum albumin concentration of 5 mg/mL). The components of the pharmaceutical composition (6) are shown in Table 1.

Figure 6:
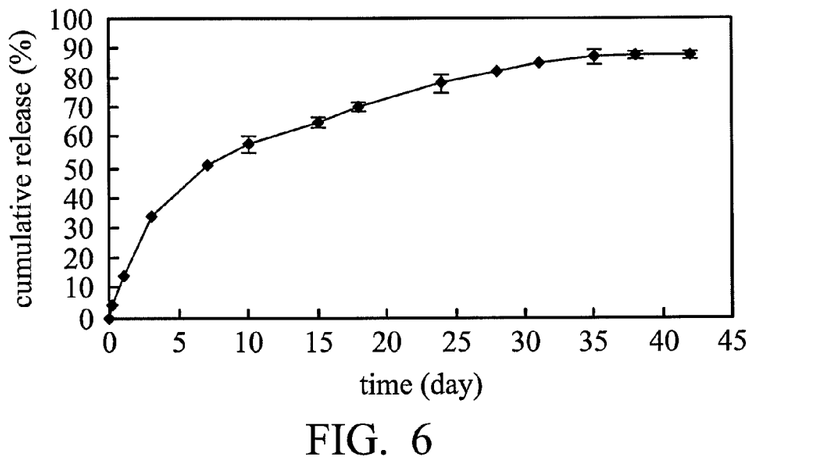
FIG. 6 shows a graph plotting cumulative release against time of the pharmaceutical composition of Example 6.

The cumulative release dose of the pharmaceutical composition (6) was measured according to the method as disclosed in Example 1 (10 mM PBS (pH 7.4) as the release medium), and the results are shown in FIG. 6. As shown in FIG. 6, the pharmaceutical composition (6) had a long-term release characteristic of more than 35 days.

Example 7

1 g of chitosan with palmitoyl groups (with a grafting rate of 20%, and a molecular weight of 500 kDa) was dissolved in 100 mL of an acetic acid aqueous solution (1%). After dialysis, the pH value of the mixture was close to pH6.2~6.5. After ultrafiltration, a solution was obtained, wherein the chitosan with palmitoyl groups had a weight percentage of 0.8 wt %. Next, an immunoglobulin G (IgG) solution (2.4 mg/mL) was mixed with the solution including the chitosan with palmitoyl groups, obtaining the pharmaceutical composition (7) (with an immunoglobulin G (IgG) concentration of 0.24 mg/mL). Particularly, the volume ratio of the immunoglobulin G (IgG)

solution and the solution including the chitosan with palmitoyl groups was 1:9. The components of the pharmaceutical composition (7) are shown in Table 1.

Figure 7:
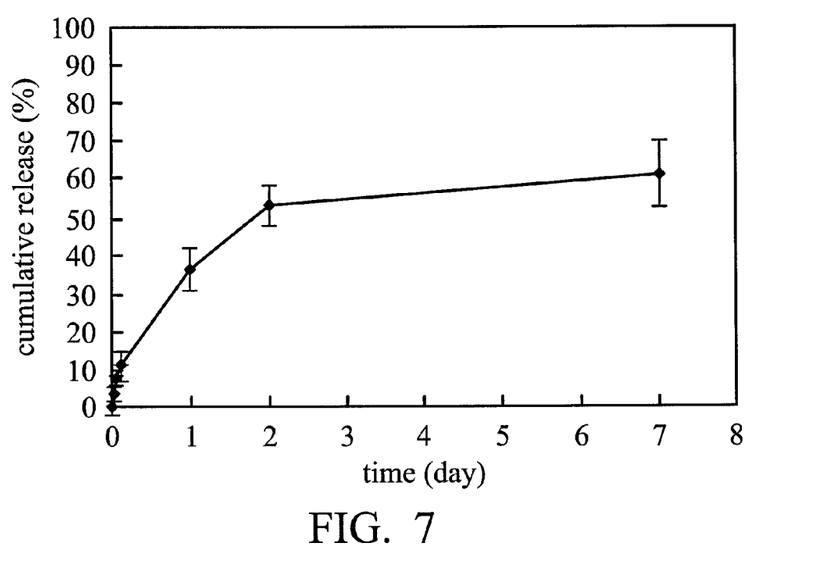
FIG. 7 shows a graph plotting cumulative release against time of the pharmaceutical composition of Example 7.

The cumulative release dose of the pharmaceutical composition (7) was measured according to the method as disclosed in Example 1 (10 mM PBS (pH 7.4) as the release medium), and the results are shown in FIG. 7. As shown in FIG. 7, the pharmaceutical composition (6) had a long-term release characteristic of more than 7 days.

TABLE 1

|  | active agent | form of active agent | weight ratio between the chitosan with palmitoyl groups and the active agent |
|---|---|---|---|
| Example 1 | paclitaxel | solution (dissolved in ethanol) | 1.44:1 |
| Example 2 | paclitaxel | nano-crystal | 1:44:1 |
| Example 3 | paclitaxel | nano-crystal | 1.2:1 |
| Example 4 | paclitaxel | nano-crystal | 1:1 |
| Example 5 | doxorubicin | liposome | 51.42:1 |
| Example 6 | bovine serum albumin | powder | 1.44:1 |
| Example 7 | immunoglobulin G (IgG) | solution | 30:1 |

Example 8

1 g of chitosan with palmitoyl groups (with a grafting rate of 22%, and a molecular weight of 500 kDa) was dissolved in 100 mL of an acetic acid aqueous solution (1%). After dialysis, the pH value of the mixture was close to pH 6.2~6.5. After ultrafiltration, a pharmaceutical composition (8) was obtained, wherein the chitosan with palmitoyl groups had a weight percentage of 0.72 wt % after dialysis and ultrafiltration.

Next, 500 µL of pharmaceutical composition (8) was loaded into circular-shaped tube and then added with the 5 mL of 10 mM PBS (pH 7.4). The bottles were placed in a shaking incubator at 37° C. and 25 rpm. The gelation time of the pharmaceutical composition (8) was measured, and the results are shown in Table 2.

Example 9

1 g of chitosan with palmitoyl groups (with a grafting rate of 22%, and a molecular weight of 500 kDa) was dissolved in 100 mL of an acetic acid aqueous solution (1%). After dialysis, the pH value of the mixture was close to pH 6.2~6.5. After ultrafiltration, a solution including the chitosan with palmitoyl groups was obtained, wherein the chitosan with palmitoyl groups had a weight percentage of 0.72 wt %. Next, γ-Poly glutamic acid (having a repeat unit of n>0) was mixed with the solution including the chitosan with palmitoyl groups, obtaining the pharmaceutical composition (9) (with the γ-Poly glutamic acid concentration of 0.25 mg/mL).

The gelation time of the pharmaceutical composition (9) was measured according to the method as disclosed in Example 8, and the results are shown in Table 2.

Example 10

1 g of chitosan with palmitoyl groups (with a grafting rate of 22%, and a molecular weight of 500 kDa) was dissolved in 100 mL of an acetic acid aqueous solution (1%). After dialysis, the pH value of the mixture was close to pH 6.2~6.5. After ultrafiltration, a solution including the chitosan with palmitoyl groups was obtained, wherein the chitosan with palmitoyl groups had a weight percentage of 0.72 wt %. Next, disodium β-glycerophosphate (having a structure represented by was mixed with the solution including the chitosan with palmitoyl groups, obtaining the pharmaceutical composition (10) (with the disodium β-glycerophosphate concentration of 14.4 mg/mL).

The gelation time of the pharmaceutical composition (10) was measured according to the method as disclosed in Example 8, and the results are shown in Table 2.

Example 11

1 g of chitosan with palmitoyl groups (with a grafting rate of 22%, and a molecular weight of 500 kDa) was dissolved in 100 mL of an acetic acid aqueous solution (1%). After dialysis, the pH value of the mixture was close to pH 6.2~6.5. After ultrafiltration, a solution including the chitosan with palmitoyl groups was obtained, wherein the chitosan with palmitoyl groups had a weight percentage of 1 wt %. Next, glycerol (having a structure represented by was mixed with the solution including the chitosan with palmitoyl groups, obtaining the pharmaceutical composition (11). Particularly, the volume ratio of the glycerol and the solution including the chitosan was 3:7.

The gelation time of the pharmaceutical composition (11) was measured according to the method as disclosed in Example 8, and the results are shown in Table 2.

TABLE 2

| | components | | |
|---|---|---|---|
| | hydrogel | gelling accelerating agent | gelation time(min) |
| Example 8 | chitosan with palmitoyl groups | — | 60-120 |
| Example 9 | chitosan with palmitoyl groups | γ-Poly glutamic acid | 30-60 |
| Example 10 | chitosan with palmitoyl groups | disodium β-glycerophosphate | 10-20 |
| Example 11 | chitosan with palmitoyl groups | glycerol | 30-60 |

Example 12

1 g of chitosan with palmitoyl groups (with a grafting rate of 22%, and a molecular weight of 500 kDa) was dissolved in 100 mL of an acetic acid aqueous solution (1%). After dialysis, the pH value of the mixture was close to pH 6.2~6.5. After ultrafiltration, a solution including the chitosan with palmitoyl groups was obtained, wherein the chitosan with palmitoyl groups had a weight percentage of 0.8 wt %. Next, a paclitaxel solution (50 mg of paclitaxel dissolved in 1 mL of ethanol) was mixed with the solution including the chitosan with palmitoyl groups, obtaining the pharmaceutical composition (12) (with a paclitaxel concentration of 5 mg/mL). Particularly, the volume ratio of the paclitaxel solution and the solution including the chitosan with palmitoyl groups was 1:9.

500 μL of pharmaceutical composition (12) was loaded into circular-shaped tube and then added with the 5 mL of 10 mM PBS (pH 7.4) containing 2.4% polysorbate 80 (manufactured by Scharlau with the trade No. of Tween 80) and 4% polyoxyethylene castor oil (manufactured by Sigma with the trade No. of Cremophor EL). The bottles were placed in a shaking incubator at 37° C. and 25 rpm. The gelation time of the pharmaceutical composition (12) was measured, and the results are shown in Table 3.

Example 13

1 g of chitosan with palmitoyl groups (with a grafting rate of 22%, and a molecular weight of 500 kDa) was dissolved in 100 mL of an acetic acid aqueous solution (1%). After dialysis, the pH value of the mixture was close to pH 6.2~6.5. After ultrafiltration, a solution was obtained, wherein the chitosan with palmitoyl groups had a weight percentage of 0.8 wt %. Next, a paclitaxel solution (50 mg of paclitaxel dissolved in 1 mL of ethanol), and γ-Poly glutamic acid were mixed with the solution including the chitosan with palmitoyl groups, obtaining the pharmaceutical composition (13) (with a paclitaxel concentration of 5 mg/mL, and a γ-Poly glutamic acid concentration of 0.25 mg/mL). Particularly, the volume ratio of the paclitaxel solution and the solution including the chitosan with palmitoyl groups was 1:9. Further, the γ-Poly glutamic acid had a weight percentage of 2 wt %, based on the total weight of the chitosan and paclitaxel.

The gelation time of the pharmaceutical composition (13) was measured according to the method as disclosed in Example 12, and the results are shown in Table 3.

Figure 8:
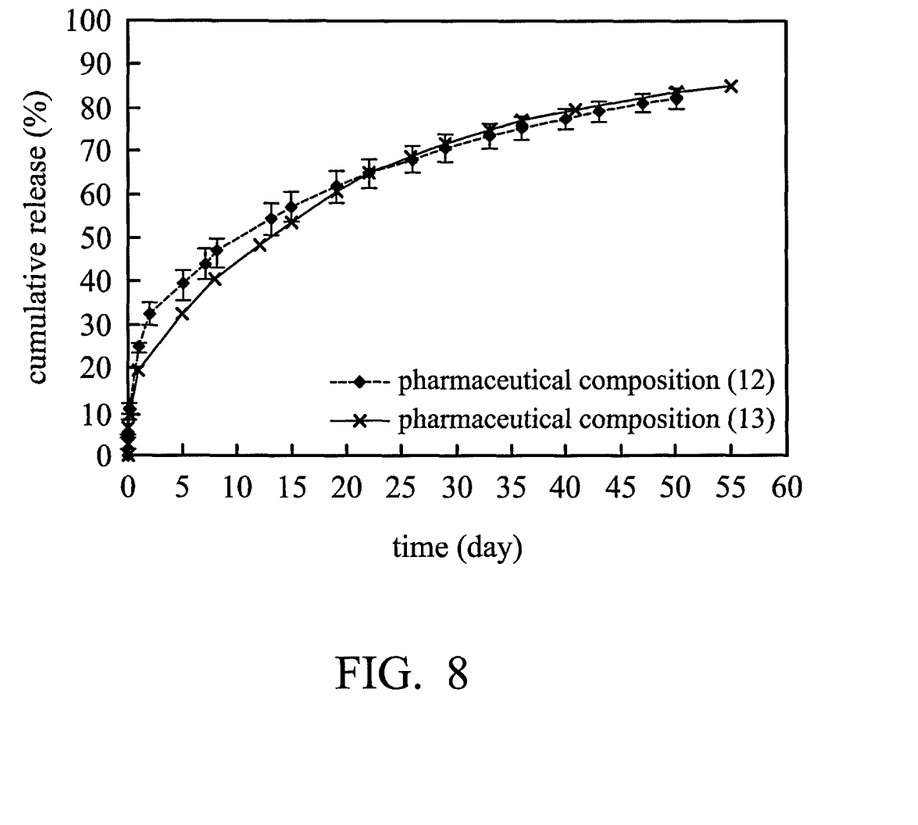
FIG. 8 shows a graph plotting cumulative release against time of the pharmaceutical compositions (12) and (13).

The cumulative release dose of the pharmaceutical compositions (12) and (13) were measured according to the method as disclosed in Example 1, and the results are shown in FIG. 8. As shown in FIG. 8, since the obtained curve of the pharmaceutical composition (12) is similar with that of the pharmaceutical composition (13), the addition of γ-Poly glutamic acid into the pharmaceutical composition of the disclosure still maintained the drug sustained release ability.

Example 14

1 g of chitosan with palmitoyl groups (with a grafting rate of 22%, and a molecular weight of 500 kDa) was dissolved in 100 mL of an acetic acid aqueous solution (1%). After dialysis, the pH value of the mixture was close to pH 6.2~6.5. After ultrafiltration, a solution was obtained, wherein the chitosan with palmitoyl groups had a weight percentage of 0.8 wt %. Next, a paclitaxel solution (50 mg of paclitaxel dissolved in 1 mL of ethanol), and disodium β-glycerophosphate (having a structure represented by were mixed with the solution including the chitosan with palmitoyl groups, obtaining the pharmaceutical composition (14) (with a paclitaxel concentration of 5 mg/mL, and a disodium β-glycerophosphate concentration of 14.4 mg/mL). Particularly, the volume ratio of the paclitaxel solution and the solution including the chitosan with palmitoyl groups was 1:9. Further, the disodium β-glycerophosphate had a weight percentage of 118 wt %, based on the total weight of the chitosan and paclitaxel.

The gelation time of the pharmaceutical composition (14) was measured according to the method as disclosed in Example 12, and the results are shown in Table 3.

TABLE 3

| | gelation time(min) |
|---|---|
| pharmaceutical composition (12) | 60-120 |
| pharmaceutical composition (13) | 30-60 |
| pharmaceutical composition (14) | 10-20 |

As shown in Table 3, the pharmaceutical composition including the γ-Poly glutamic acid (or disodium β-glycerophosphate) had a relative high gelation rate, in comparison with the pharmaceutical composition without the γ-Poly glutamic acid (or disodium β-glycerophosphate).

Example 15

1 g of chitosan with palmitoyl groups (with a grafting rate of 22%, and a molecular weight of 500 kDa) was dissolved in 100 mL of an acetic acid aqueous solution (1%). after dialysis, the pH value of the mixture was close to pH 6.2~6.5. After ultrafiltration, a solution including the chitosan with palmitoyl groups was obtained, wherein the chitosan with palmitoyl groups had a weight percentage of 0.9 wt %.

Next, a paclitaxel solution (50 mg of paclitaxel dissolved in 1 mL of ethanol) was mixed with the solution including the chitosan with palmitoyl groups, obtaining the mixture. Particularly, the volume ratio of the paclitaxel solution and the solution including the chitosan with palmitoyl groups was 1:9. Next, a glycerol was mixed with the mixture, obtaining the pharmaceutical composition (15) (with a paclitaxel concentration of 5 mg/mL). Particularly, the volume ratio of the glycerol and the mixture was 1:9.

Figure 9:
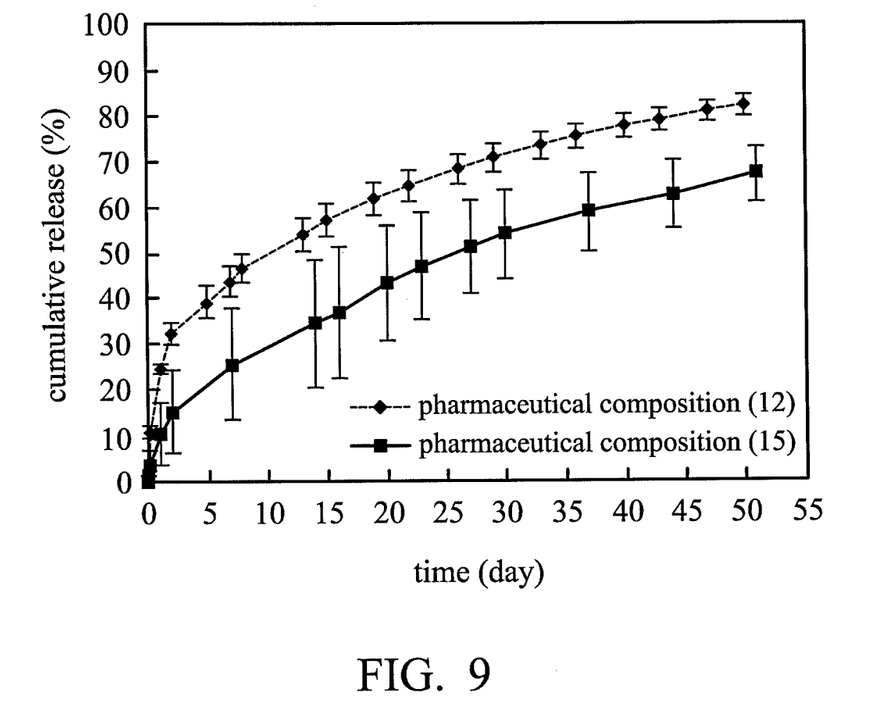
FIG. 9 shows a graph plotting cumulative release against time of the pharmaceutical compositions (12) and (15).

The cumulative release dose of the pharmaceutical compositions (12) and (15) were measured according to the method as disclosed in Example 1, and the result is shown in FIG. 9. As shown in FIG. 9, the release rate of the pharmaceutical composition including the glycerol was 2.7 times slower than that of the pharmaceutical composition without the glycerol under the condition when 50% of the active agent was released.

Accordingly, the pharmaceutical composition of the disclosure has long-term release characteristics of more than 7 days. Further, in the Examples, some of the pharmaceutical compositions of the disclosure had long-term release characteristics of more than 28 days.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A pharmaceutical composition, comprising:
    a chitosan with palmitoyl groups;
    an active agent, wherein the chitosan with palmitoyl groups has a weight percentage of 50-98.5 wt %, and the active agent has a weight percentage of 1.5-50 wt %, based on the total weight of the chitosan with palmitoyl groups and the active agent; and
    a gelling accelerating agent, wherein the gelling accelerating agent comprises a lipid.

2. The pharmaceutical composition as claimed in claim 1, wherein the active agent is in the form of a nano-drug, liposome, micelle, or microparticle.

3. The pharmaceutical composition as claimed in claim 1, wherein the pharmaceutical composition comprises 2-120 parts by weight of the gelling accelerating agent, and 100 parts by weight of the sum of the chitosan with palmitoyl groups and the active agent.

4. The pharmaceutical composition as claimed in claim 2, wherein the chitosan with palmitoyl groups is a chitosan grafted with palmitic acid N-hydroxysuccinimide ester at a grafting ratio of 5-25%.

5. The pharmaceutical composition as claimed in claim 2, wherein the active agent comprises a hydrophilic active agent, hydrophobic active agent, or combinations thereof.

6. The pharmaceutical composition as claimed in claim 5, wherein the hydrophobic active agent comprises a paclitaxel, docetaxel, or combinations thereof.

7. The pharmaceutical composition as claimed in claim 5, wherein the hydrophilic active agent comprises a cisplatin, doxorubicin, bovine serum albumin, immunoglobulin G (IgG), or combinations thereof.

* * * * *